(12) United States Patent
Butterfield et al.

(10) Patent No.: US 6,554,806 B2
(45) Date of Patent: Apr. 29, 2003

(54) BURETTE SAFETY VALVE

(75) Inventors: Robert D. Butterfield, Poway, CA (US); Emmet B. Anderson, Santee, CA (US)

(73) Assignee: Alaris Medical Systems, Inc., San Diego, CA (US)

(*) Notice: Subject to any disclaimer, the term of this patent is extended or adjusted under 35 U.S.C. 154(b) by 34 days.

(21) Appl. No.: 09/777,788

(22) Filed: Feb. 5, 2001

(65) Prior Publication Data

US 2002/0107490 A1 Aug. 8, 2002

(51) Int. Cl.⁷ .............................................. A01M 5/14
(52) U.S. Cl. ............................ 604/248; 604/250; 251/9
(58) Field of Search ....................... 604/80, 248, 251, 604/32, 250; 251/4, 9

(56) References Cited

U.S. PATENT DOCUMENTS

| | | | |
|---|---|---|---|
| 3,016,915 A | 1/1962 | Moeller, Jr. | 137/595 |
| 3,216,418 A | 11/1965 | Scislowicz | 128/214 |
| 3,411,534 A | 11/1968 | Rose | 137/595 |
| 3,776,229 A | 12/1973 | McPhee | 128/214 C |
| 3,918,490 A | 11/1975 | Goda | 137/59 |
| 4,177,969 A | 12/1979 | Sieber-Müller | 251/9 7 |
| 4,484,599 A | 11/1984 | Hanover et al. | 137/636 |
| 4,553,964 A | 11/1985 | Sasaki | 604/248 |
| 4,660,802 A | 4/1987 | Oscarsson | 251/9 |
| 5,853,398 A | 12/1998 | Lal et al. | 604/250 |
| 5,989,223 A | 11/1999 | Chu et al. | 504/167 |

FOREIGN PATENT DOCUMENTS

DE        87 14 457 U        12/1987

Primary Examiner—Philippe Derakshani
(74) Attorney, Agent, or Firm—Fulwider Patton Lee & Utecht, LLP

(57) ABSTRACT

A system for controlling fluid flow through multiple conduits for use in a fluid administration device. The system includes a housing, a cam, and a control element used to move the cam to selectively occlude the conduits. When used with a medical burette, the cam is located between the vent and supply conduits and rotates to alternately occlude one or the other conduits or to leave both conduits patent. Depending on the rotational position of the cam, the continuous flow mode, the intermittent flow mode, and the priming mode are all obtained with a single control lever. The housing secures the conduits in predetermined, fixed positions both above and below the contact location of the cam to the conduit. A positive locking device is included to assist in locating the cam in the desired position. Clear visual indicators are included on the housing for viewing the present flow operating state.

38 Claims, 5 Drawing Sheets

BURETTE SAFETY VALVE

BACKGROUND

The present invention relates to an improved valve system for controlling fluid flow through multiple conduits and, in particular, to a safety valve for use in the administration of medical fluids to patients.

Medical procedures often require introducing fluids into a patient using systems such as parenteral administration sets. Many of these administration sets include multiple, independently operated clamps or valves that control the flow of fluids through the administration set and into the patient. Such sets generally include a vent conduit and at least one supply conduit connected to a supply container such as a fluid-filled bag. To dispense the fluid, a medical operator or other user manually employs the clamps as needed to close or open the conduits of the administration set during the fluid administration. These administration sets may also include injection ports to introduce additives such as antibiotics or other medicaments into the administration solution, as required.

In one medical application, an administration set is used to continuously feed a steady and continuing flow of saline, dextrose or other solution from the supply container intravenously to the patient. The amount fed is limited by the amount in the supply container. In other medical procedures, a precise volume less than the total supply container volume must be fed to the patient over a single flow period. For this volumetric use, the administration set may include a burette chamber in the flow path that may be used to more precisely measure a prescribed volume of solution. In this arrangement, the solution flows from the supply container to the burette chamber to be measured and then to the patient. Depending on the means used to cause the fluid to flow downstream to the patient, an intermediate chamber, such as a drip chamber, may be placed in the flow path downstream of the burette chamber so that fluid flow may be monitored and timed.

In the use of administration sets, it is typical to prime the set before use to eliminate any air that may be harmful to the patient. The valves and clamps of the administration set, including any associated with the burette chamber, must be activated appropriately to assist in entering the priming mode of the administration set. In the priming mode, fluid from the supply container is channeled into the calibrated burette chamber. Typically, individual conduit clamps of the burette chamber are separately manipulated so that both vent and supply conduits are open which allows the source fluid to flow into the burette chamber and to vent the displaced air out the vent conduit. Another clamp may then be used to prime the rest of the administration set conduits and to control the fluid flow through the system.

Once primed, the operator may place the administration set having a burette chamber into the intermittent flow mode which delivers only the medical fluid in the burette chamber to the patient by releasing the vent conduit and closing the supply conduit. The precise amount of fluid that has been measured by the operator with the burette chamber is then administered to the patient. Alternately, the operator may place the administration set into a continuous flow mode by opening the supply conduit to the desired flow level and closing the vent conduit so that the flow of fluid from the supply container is continuous.

Burette chambers typically have an upstream supply conduit through which fluid from a supply source flows into the burette chamber. Burette chambers also typically have an upstream vent conduit through which air in the burette chamber may be vented to the outside as the chamber is filled with fluid from the supply source. Both of these upstream conduits may be clamped shut or may be opened as needed for the flow mode desired. As described above, many administration sets having a burette chamber providing for the priming mode, intermittent flow mode, and continuous flow mode require a particular arrangement of conduit clamps to close or open the upstream vent and supply conduits. These arrangements can become troublesome and inconvenient to an operator. It is necessary for the operator to remember which valve or valves must be open and which must be closed for the particular flow mode desired. Failure to correctly set the valves can result in another mode being configured rather than the one desired.

An effective medical burette administration set must be designed for safety and ease of operation. Preferably, the set includes a safety system that would prevent both upstream conduits (supply and vent conduits) from being simultaneously closed, known as a "closed-closed" flow mode. Such a condition could result in a partial vacuum being formed in the administration set and the burette chamber that could potentially slow or interrupt fluid delivery to the patient or in a worse case, pull blood from the patient's catheter subsequent to the set being removed from an infusion pump. Drawing blood from the catheter presents a risk to the patient of possible clotting or damage to the vessel in the region of the catheter tip. A preferred design would also take measures to avoid contamination to the operator, such as smooth design features that do not tear gloves worn by the operator. Additionally, a preferred design would include unambiguous visual indicators used to gage the flow configuration of the system. These indicators minimize the risk of accidental placement of the administration set into an inadvertent operating state. Known administration sets have certain design limitations that have not entirely overcome these concerns.

U.S. Pat. No. 5,853,398 to Lal et al. proposes a flow-adjusting clamp system in a burette administration set to select the described flow modes and avoid the "closed-closed" flow mode. In the Lal system, a dual-slotted cam mounted at the input end of the burette functions as a selective clamp by closing off flow alternately through the two flexible conduits running through each slot of the cam. One conduit is a vent conduit while the other is a conduit from the fluid reservoir. The slots in the cam vary between a narrow opening and a wide opening. The narrow opening is used for closing off or occlusion of the conduit while the wide opening is used for unrestricted flow. The medical operator grasps the edge of the cam to manually pivot the cam to a selected rotational position. As the cam pivots horizontally, the vertical conduits slide laterally along the open unrestrictive portions and the closing portions of the slots. The edges of the narrow portions of the slots close off flow through the conduits. The wider portions of the slots release flow through the conduits. The slots are aligned so that at any cam position, both slots will not be closed simultaneously as long as the conduits remain in the vertical position. While the medical operator pivots the dual slotted cam through a predetermined arc, the edges of the slots restrict and release the vent and supply conduits to select the priming, intermittent and continuous flow modes.

Administrative sets that use a horizontal dual-slotted cam system potentially introduce operational problems to medical personnel. In order to accurately control flow, the conduits must remain vertically fixed while laterally sliding along the slots to maintain the same rotational position. Below the pivoting cam, the conduits are held in a substantially fixed position by their connections to the burette cap. However, above the pivoting cam, the system does not restrict movement of the flexible conduits which potentially allow the conduits to move from the vertical position. If the pivoting cam is not mounted close enough to the burette cap and if the conduits move from a vertical position such as by bending in response to the narrow slots of the slotted cam, the narrow portion of a cam slot may not fully engage the conduit and full occlusion may not occur. The medical operator may have to manually arrange the conduits in the cam slots or hold the conduits steady while the cam is rotated to correct the flow mode. Arranging the conduit while pivoting the dual-slotted cam could prove difficult to a medical operator wearing protective gloves. The medical operator could potentially tear the gloves while trying to orient the cam and conduits in the correct alignment. Moreover, the medical operator could err in the placement of the conduits within the cam and apply an inadvertent flow mode. Introducing this possible need for manual control into use of the cam is undesirable.

Additional complications may arise in using this system due to the difficulty in reading the operating state or flow mode of the system from a distance. To accurately determine the operating state of the system, the medical operator or other personnel must see the location of the conduits within the dual-slotted cam. Since the cam is horizontally located on top of the burette cap, a medical operator would have to look down on the system from a close distance to read the operating state. This arrangement makes it more difficult to use and less versatile.

Hence those skilled in the art have recognized a need for an improved burette administration set. Another need recognized is for a safety valve capable of placing a burette fluid administration set in the priming, intermittent, and continuous flow modes while avoiding the "closed-closed" flow mode. Such a system should restrict the movement of the conduits to avoid inadvertent operating states of the system. The system should also be relatively easy to use by providing a single control element that is readily visible and assessable to the medical operator. Additional visual indicators should be provided to allow the medical operator to view the operating state of the system from a distance. The invention fulfills these needs and others.

SUMMARY OF THE INVENTION

The invention in one aspect is directed to a system for controlling fluid flow through multiple conduits. The system comprises a housing in which the conduits are held in predetermined, fixed positions, a cam rotatably disposed within the housing and mounted so as to permit controlled, alternate compression contact of an external surface of the cam with each of the conduits to restrict flow therein, and a control element operably connected to the cam to selectively position the cam into contact with each of the conduits, wherein the housing secures the conduits against movement at positions both above and below the contact locations of the cam with the conduits.

In more detailed aspects, the cam is mounted so that it rotates about an axis that is perpendicular to longitudinal axes of the conduits. The housing receives the conduits so that the housing provides support for each conduit generally surrounding the area of compression contact with the cam. The cam is located between the conduits. The housing comprises a stop surface that is located to prevent the cam from rotating through a predetermined arc. The housing comprises a visual indicator visible from a position external to the housing to disclose the position of the cam in relation to the conduits.

In yet further aspects, the control element comprises a handle disposed on the outside of the housing, the handle aligned with the cam in a predetermined manner to indicate the position of the cam. The handle is aligned with the cam to indicate a flow operating state of a conduit. The handle is aligned with the cam to indicate that a conduit is occluded. An indicator is disposed on the outside of the housing so that aligning the handle with the indicator discloses a flow operating state of a conduit.

In other detailed aspects, the system further comprises a positioning device located within the housing for controllably holding the cam at a predetermined position. The positioning device comprises a detent. The positioning device further comprises a spring-loaded aligning device located on one of the cam or the housing and the detent is located on the other of the cam or the housing. The spring-loaded aligning device comprises a ball bearing, and a spring, the spring located so as to urge the ball bearing into the detent so that the cam will controllably remain in a predetermined position at the detent. In a further aspect, the system comprises a plurality of positioning devices located within the housing for controllably holding the cam at predetermined positions in relation to the conduits.

In more detailed aspects, the cam is solid. The cam rotates about an axis located parallel to longitudinal axes of the conduits.

In accordance with other aspects, the invention is directed to a medical burette having an upstream end and a downstream end interconnected by a burette chamber, the burette chamber having a longitudinal axis, the burette comprises a housing disposed at the upstream end of the burette, the housing having a vent conduit, and a supply conduit, the conduits held in fixed positions within the housing and in fluid communication with the chamber, a cam rotatably mounted within the housing between the vent conduit and the supply conduit, the cam mounted within compression contact range of both the conduits such that the cam may selectively be rotated to occlude either of the conduits, a control element connected to the cam for rotating the cam to selectively occlude the conduits, and the control element connected to the cam such that the control element has an indicator function of the position of the cam in regard to the occlusion of the conduits.

In more detailed aspects related to the burette, the cam is mounted so that it rotates about an axis that is perpendicular to longitudinal axes of the conduits. The housing receives the conduits so that the housing provides support for each conduit generally surrounding the area of compression contact with the cam. The housing comprises a stop surface located to prevent the cam from rotating through a predetermined arc. A positioning device is located within the housing for controllably holding the cam at a predetermined position in relation to a conduit. The positioning device comprises a detent. The positioning device further comprises a spring-loaded aligning device located on one of the cam or the housing and the detent is located on the other of the cam or the housing. The spring-loaded aligning device comprises a ball bearing, and a spring, the spring located so as to urge the ball bearing into the detent so that the cam will controllably remain in a predetermined position at the detent. In yet further aspects, the medical burette further comprising a plurality of positioning devices located within the housing for controllably holding the cam at predetermined positions in relation to the conduits.

In more detailed aspects, the cam is solid. The cam rotates about an axis located parallel to longitudinal axes of the conduits. The cam is mounted so that it may be rotated to a position at which neither conduit is occluded. The burette further comprises indicators at an exterior surface of the housing, the indicators adapted to signal a state of fluid flow of the burette.

In accordance with aspects of a method in accordance with the invention, there is provided a method for controlling fluid flow through multiple conduits into a burette, the burette having a housing disposed at an upstream end, the method comprising positioning the conduits in spaced-apart, fixed positions in the housing, rotating a cam disposed within the housing into compressive contact of an external surface of the cam with each of the conduits to restrict flow therein, and controlling the rotation of the cam with an external control element, and securing the conduits against movement at positions both above and below the contact locations of the cam with the conduits.

In more detailed aspects, rotating the cam comprises rotating the cam about an axis that is perpendicular to longitudinal axes of the conduits. Positioning the conduits comprises locating the conduits in the housing so that housing provides support for each conduit generally surrounding the area of compression contact with the cam. The method further comprises the step of controllably holding the cam at a selected position such that inadvertent rotation of the cam from the selected position is resisted. Holding the cam comprises locating a positioning device partially within the housing and partially within the cam such that rotation of the cam is resisted. The method also comprises in a more detailed aspect biasing the positioning device into the location partially within the housing and partially within the cam. Rotating the cam comprises rotating the cam about an axis that is parallel to longitudinal axes of the conduits.

A more detailed aspect in accordance with the method of the invention includes indicating at an exterior surface of the housing the state of fluid flow of the burette.

Other features and advantages of the invention will become more apparent from the following detailed description of preferred embodiments of the invention, when taken in conjunction with the accompanying exemplary drawings.

DETAILED DESCRIPTION OF THE PREFERRED EMBODIMENTS

Figure 1:
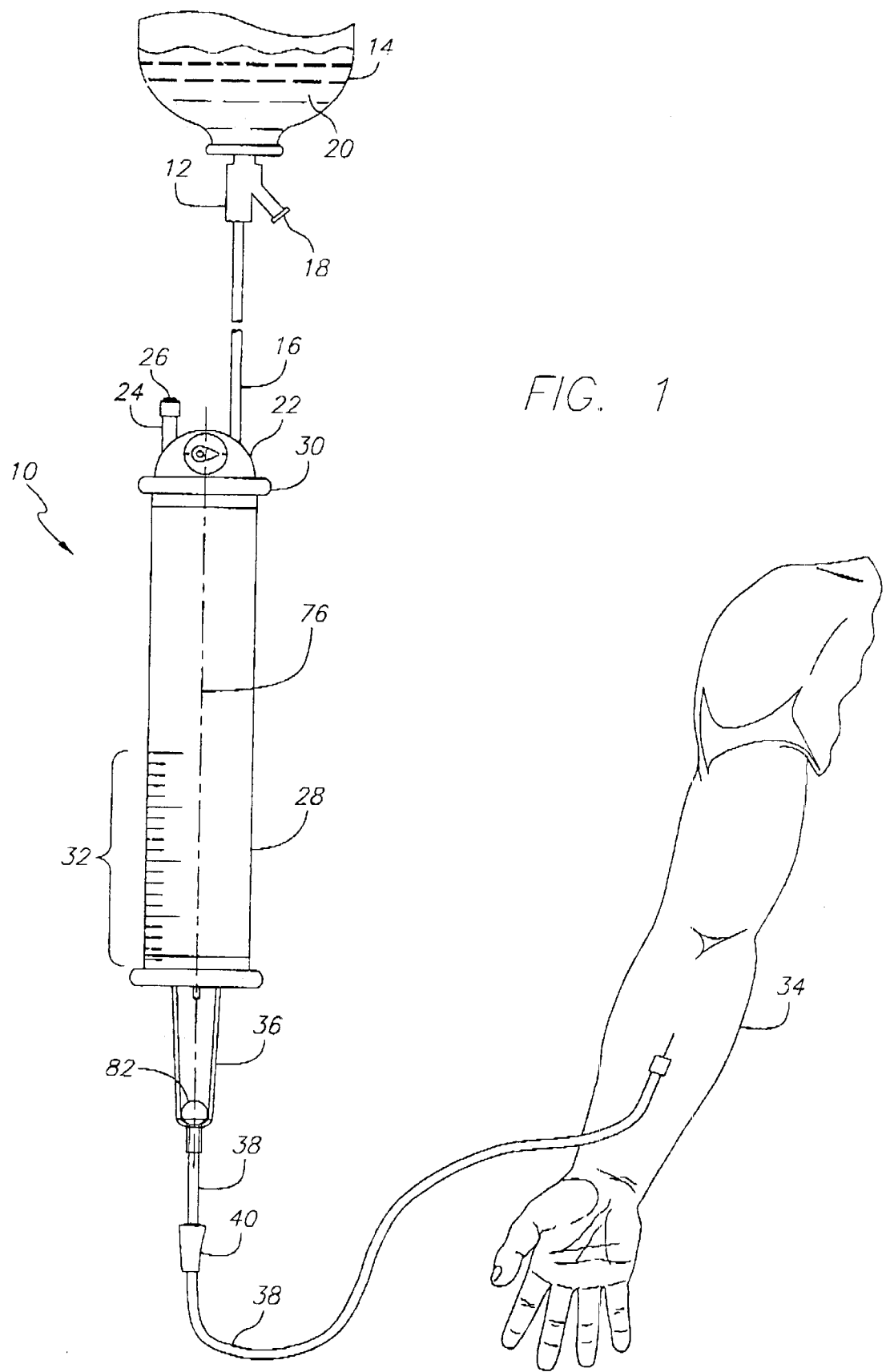
FIG. 1 is a view of an administration system connected between a fluid reservoir and a patient and includes a burette, drip chamber, and a downstream clamp, the burette including a system for controlling fluid flow through multiple conduits in accordance with aspects of the present invention.

In the following description, like reference numerals are used to refer to like or corresponding elements in the different figures of the drawings. Referring now to the drawings with more particularity, FIG. 1 shows a parenteral administration set 10 for intravenously introducing medical fluids into a patient. As is well known to those skilled in the art, the spike 12 used to interconnect the supply container 14 with the supply conduit 16 includes a vent 18 thus permitting continuous flow of medical fluid 20 from the supply container 14 through the supply conduit 16 into a fluid flow control system 22. A flexible bag or other type of reservoir may be used instead of the supply container 14 to make storage of the fluids easier. A vent conduit 24 is also connected to the fluid flow control system 22. A filter 26 is attached to the end of the vent conduit 24 to screen contaminants. The fluid flow control system 22 is mounted on a burette chamber 28 and controls or regulates fluid communication between the chamber 28 and the supply conduit 16 and the vent conduit 24 though openings formed in the top of the burette cap 30. Preferably, the burette chamber 28 has calibration marks 32 that allow the medical operator to measure a prescribed volume of fluid to be intravenously released into the patient 34. In this arrangement, medical fluid 20 flows from the burette chamber 28 into an intermediate drip chamber 36 and then through the downstream conduit 38 before entering the patient 34. A roller clamp 40 engaged with the downstream conduit 38 downstream of the drip chamber 36 may be used to shut off the fluid flow from the burette chamber 28 into the patient 34.

In prior administration sets, the medical operator would have to manipulate a roller clamp on the supply conduit 16 and the downstream roller clamp 40 on the downstream conduit 38 to control the flow of the medical fluid 20 through the administration set 10. The medical operator would also have to adjust another clamp or valve on the vent conduit 24 depending on the flow mode desired. To obtain the desired flow mode, the medical operator would need to remember the particular arrangement of clamps, which number three in this prior art example. Additionally, the operator needs to remember that both valves on the supply conduit 16 and the vent conduit 24 should not be closed simultaneously during operation to avoid the "closed-closed" condition.

Figure 2:
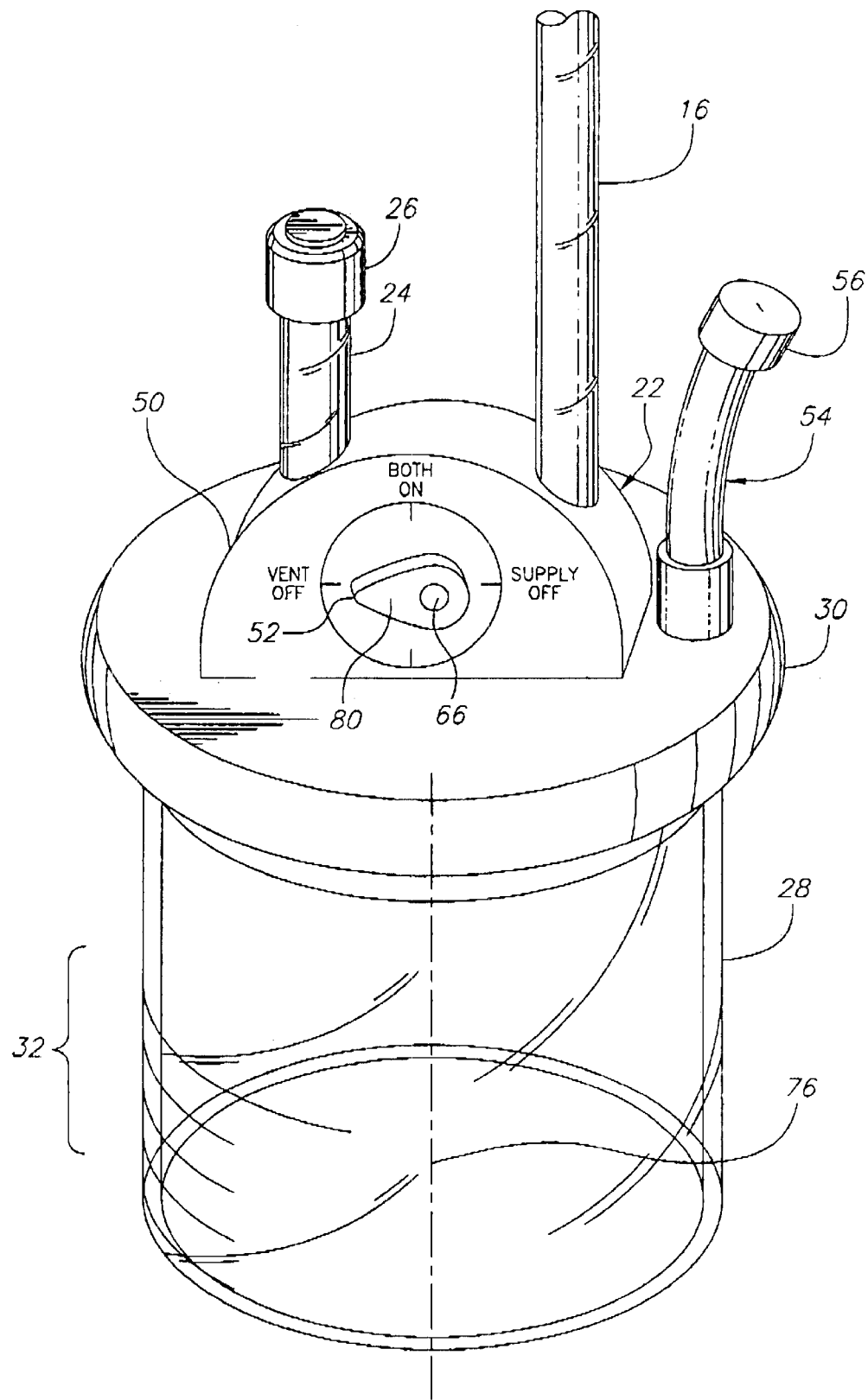
FIG. 2 is a front perspective view of the upstream of a burette having a system for the control of fluid through multiple conduits mounted on its cap in accordance with aspects of the present invention showing a vent conduit and a supply conduit controlled by the present system.

Individual components comprising the fluid flow control system 22 for controlling fluid flow through the input conduit 16 and the vent conduit 24 to the burette are shown in more detail in the perspective view of FIG. 2. The fluid flow control system 22 includes a housing 50, an internal solid cam (not shown) enclosed within the housing 50, and a control element 52 for rotating the solid cam into compression contact with either the supply conduit 16 or the vent conduit 24 separately to alternatively restrict the fluid flow therein, as described in greater detail below. The control element 52, such as a handle or a lever, is located outside the housing 50 for ease of access. The control element 52 or lever arm is blunt so as not to puncture the gloves or skin of the medical operator. The housing 50 not only protects the housed components of the fluid flow control system 22 from the medical operator and foreign items, but also protects the medical operator from any components enclosed within the housing 50 that may puncture the protective gloves worn by the medical operator. The control element 52 may also be configured to indicate the flow mode selected. Through judicious use of indicia, it may visibly indicate to an observer whether the supply conduit and/or the vent conduit are open into the burette chamber 28. This feature is discussed in further detail below.

In an embodiment shown in FIG. 2, an injection port 54 with a cap 56, such as a rubber septum, may be attached to the burette cap 30 to allow a medical operator to introduce additives such as antibiotics into the burette chamber 28 and into the patient. Such an injection port 54 is a standard item on many medical burette systems. In some instances, the cap 30 of the injection port 54 is the resealable type. In such case, the medical operator may insert the blunt cannula of a syringe through the cap 56 and that cap will reseal itself after the blunt cannula has been withdrawn.

In the embodiment shown in FIG. 2, both the vent conduit 24 and the supply conduit 16 are disposed through the housing 50 in the fluid flow control system 22. The conduits 16, 24 are in fluid communication with the burette chamber 28 in that the end of each conduit 16, 24 opens up into the burette chamber 28. In this arrangement, the supply conduit 16 may be used to deliver medical fluid 20 (FIG. 1) to the burette chamber 28 as permitted by the fluid flow control system 22. Additionally, the open or closed state of the vent conduit 24 is controlled by the fluid flow control system 22.

Figure 3:
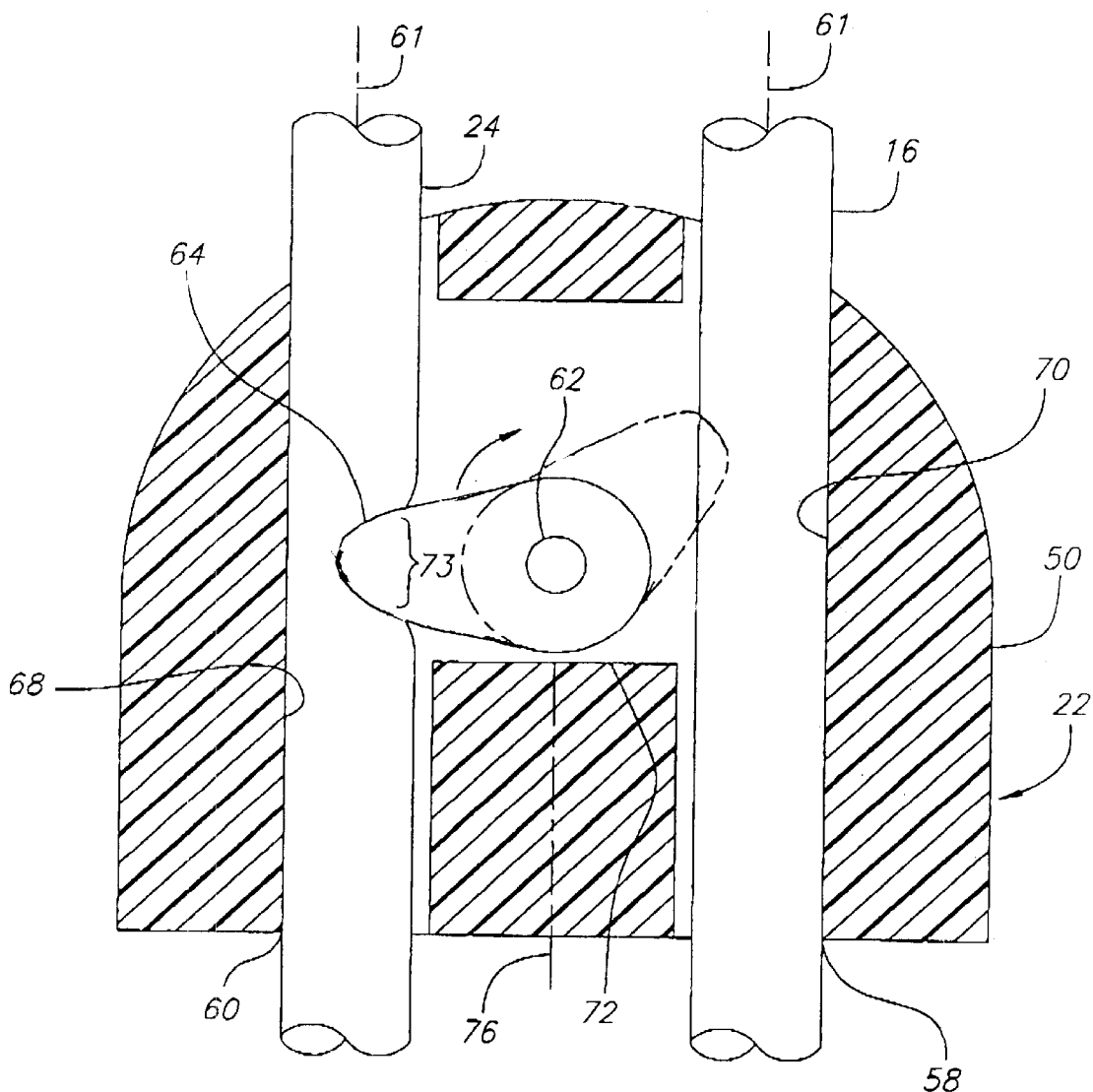
FIG. 3 is a front, partially-sectional view of the fluid flow control system of FIG. 2 where the cam within the housing has been rotated to result in the continuous flow mode in which the supply conduit is patent and the vent conduit is occluded.

The front partial sectional view of FIG. 3 shows details of internal components located within the housing 50 of the embodiment of the fluid flow control system 22 shown in FIG. 2. The housing 50 is shown in a sectional view in this case. The housing 50 includes two channels 58 and 60 that receives the two conduits 16 and 24 respectively. As will be noted by reference to FIG. 3, the two channels are disposed on either side of a solid cam 62. In this embodiment, the conduits 16 and 24 are held in position within the housing 50 to prevent them from shifting out of contact range of the rotating solid cam 62. By holding the conduits 16 and 24 in a fixed position, an external edge or lobe 64 of the solid cam will contact each conduit 16 and 24 at a desired contact point. As shown in FIG. 3, the cam 65 has been rotated to cause compression contact of an external surface 65 of the cam 62 with the conduit 24 to restrict the flow therein. As shown, the solid cam 62 is rotatably mounted to the housing 50 by means of a pivot pin 66. The solid cam 62 is fixed to the pivot pin 66 which in turn is connected to the housing 50 to maintain rotational mobility.

On the outside of the housing 50, the control element 52 from FIG. 2 is fixed to the pivot pin 66 so that the control element and the solid cam 62 move together. That is, when the medical operator rotates the control element 52 from outside the protective housing 50, the cam with move with the control element. The cam 62 may be positioned to selectively compress into occlusion either of the supply or vent conduits 16 or 24 separately in order to pinch off flow therein, or may be positioned so that it does not occlude either of the conduits 16, 24 so that both conduits are open. In FIG. 3, the vent conduit 16 is compressed into occlusion between the lobe 64 of the solid cam 62 and the pressure wall 68 of the vent conduit channel 60. The pressure wall as used herein refers to the wall of the channel of the respective conduit that is disposed opposite the cam. Also shown in dashed lines in FIG. 3 is the cam 62 rotating towards the supply conduit 16 to occlude it against its respective channel 58 pressure wall 70.

Additionally, the embodiment shown in FIG. 3 includes a stop surface 72 formed as part of the housing 50 to prevent the medical operator from rotating the cam 62 downwardly towards the burette chamber 28. The cam is therefore confined to rotation through a predetermined arc, in this case, an arc of 180 degrees. In this way, the medical operator will be prevented from selecting certain solid cam 62 positions.

Figure 4:
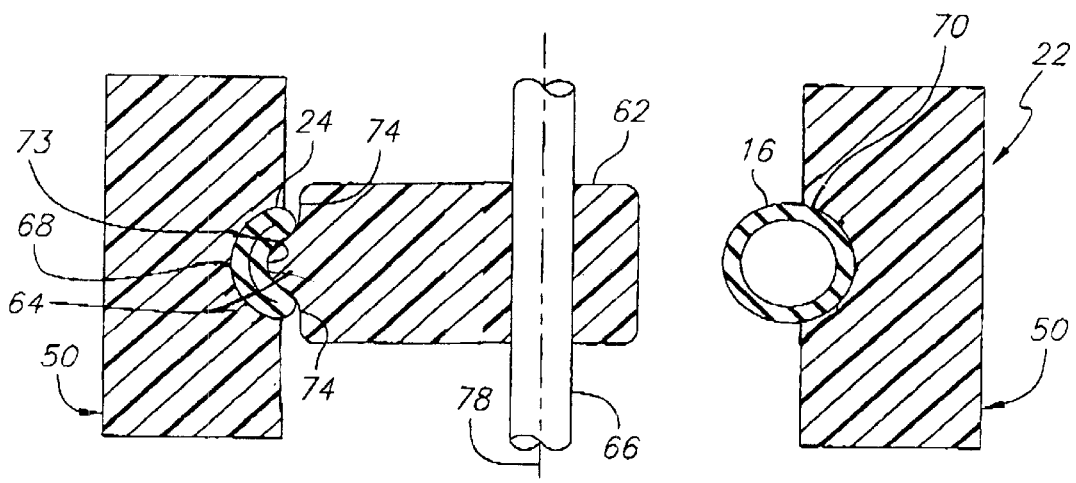
FIG. 4 is a top, partial-sectional and schematic view of the fluid flow control system of FIG. 3 in accordance with aspects of the present invention where the cam is in compression contact with the vent conduit which is preferably held in place by a concavity within the housing wall.

Referring now to FIG. 4, a top, partial sectional view is presented in which the occluding action of the cam 62 against the vent conduit 24 as shown in FIG. 3 can be seen from an angle rotated ninety degrees from that shown in FIG. 3. The housing 50 exterior walls are shown in section; however, various other details have been excluded for purposes of clarity in illustrating certain structure. The pressure walls 68 and 70 include concave-shaped portions for receiving their respective conduit. On either side of the concave portion are flat portions. The cam lobe 64 is shown occluding the vent tube 24 and as is apparent, the cam lobe has a complementary shape to the concave portion of the pressure wall 68 of the vent tube channel 60. Although other shapes are possible, the cam lobe has a center curved portion 73 that is complementary to the pressure wall 68 and also has adjoining flat portions 74 on either side of the curved portion. As can be seen by closer reference to FIG. 4, these adjoining flat portions 74 also apply pressure to the captured conduit to assist in occluding the conduit. The cam 62 is shown mounted to the pivot pin 66 as in FIG. 3. The depth of the concave portions of the pressure walls has been selected in the embodiment of FIG. 4 to provide a predetermined arc of less than 180°. The lobe 64 of the cam 62 has a thickness that is less than the diameter of the conduits 16, 24 so that the center curved portion of the lobe 64 can wedge into the center of the conduits 16, 24 fixed within the concave portions of the pressure walls 68 and 70.

The flow mode shown in both FIGS. 3 and 4 is that known as the "continuous" flow mode as fluid will be drawn directly from the supply container 14 (FIG. 1). The vent conduit 24 is occluded while the supply conduit 16 is open. Typically in such a flow mode, the burette chamber 28 is not used to measure a particular amount of medicament but is instead merely a larger diameter part of the continuous flow path.

Turning now to the orientation of the cam 62 mounting, reference to FIG. 1 and FIG. 3 shows a longitudinal axis 76 through the burette chamber 28 and the fluid flow control system 22. The supply conduit 16 and the vent conduit 24 are mounted parallel to this axis in FIG. 3. The location of the pivot pin 66 for the cam is also located along this axis; however, it is not parallel to it in the embodiment of FIGS. 3 and 4. In fact, the pivot pin axis 78 is disposed so that it is perpendicular to the burette chamber 28 axis 76.

In a preferred embodiment shown in FIG. 3 and FIG. 4, the cam 62 is oriented to rotate about a horizontal axis that is perpendicular to the longitudinal axes 68 of the conduits 16, 24 and is perpendicular to the longitudinal axis 70 of the burette chamber 28 of FIG. 1. In an alternate embodiment, the solid cam 62 rotates about a vertical axis that is parallel to the longitudinal axes 68 of the conduits 16, 24 and the burette chamber axis 76. In the embodiment shown in FIGS. 3 and 4, the solid cam 62 is located between the conduits 16, 24.

Returning briefly to FIG. 2 and with reference to FIG. 3, the control element 52 shown in FIG. 2 is mounted at one of its ends to the pivot pin 66 and therefore has an extended handle portion 80 that extends from the mounting end. In the embodiment shown in FIG. 2, the handle portion 80 is aligned with the lobe 64 of the solid cam 62 so that pointing the handle portion towards a conduit indicates that the same conduit is being occluded by the internal cam 62. The handle portion 80 therefore also acts as an indicator of which conduit is affected. However, the control element 52 could instead be mounted in the opposite direction so that it would therefore indicate that the conduit to which it is pointing is patent. In this latter arrangement, the control handle would point in the downstream direction in the priming mode and may thereby indicate that fluid may flow downstream through the administration set.

Figure 5:
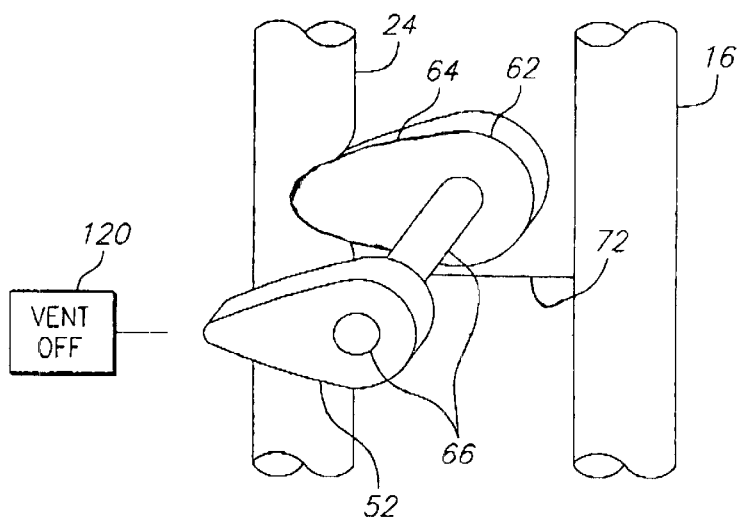
FIG. 5 is a front schematic view showing the aligned position of the cam lobe and the control element which in this case is a handle and which are interconnected by a pivot pin. The cam is shown occluding the vent conduit while the supply conduit is open for achieving the continuous flow mode.
Figure 6:
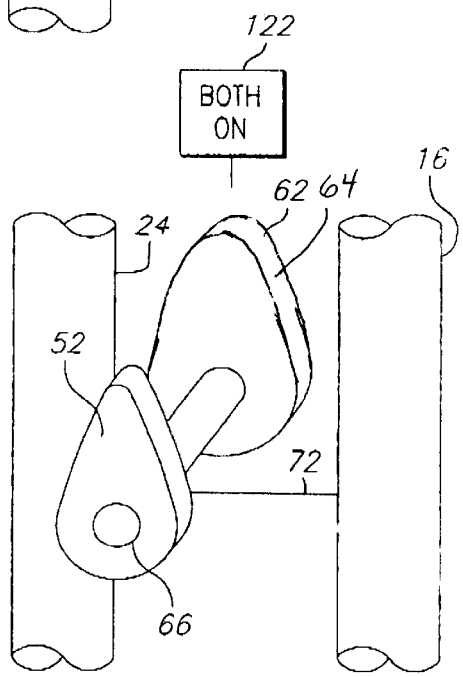
FIG. 6 is a front schematic view showing both the cam lobe and the control element rotated to face upstream so that neither the vent conduit nor the supply conduit are occluded and the priming mode is achieved.
Figure 7:
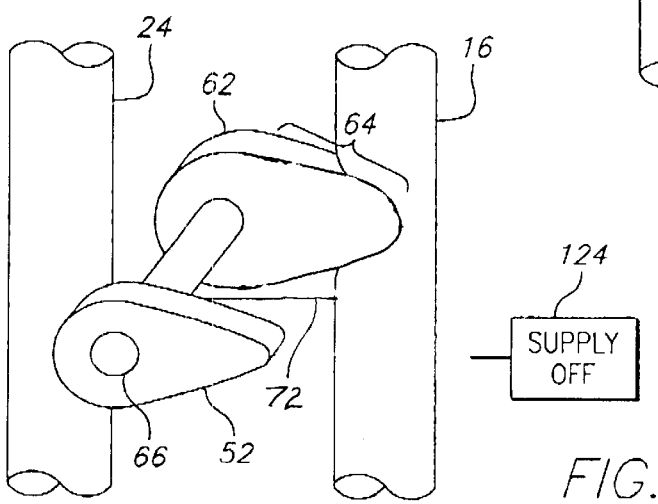
FIG. 7 is a front schematic view showing the cam lobe occluding the supply conduit while the vent conduit is open for achieving the intermittent flow mode.

Turning now to the schematic diagrams of FIG. 5, FIG. 6, and FIG. 7, the medical operator may rotate the solid cam 62 through a 180 degree arc from the continuous mode shown in FIG. 5 where the vent conduit 24 is occluded but the supply conduit is patent, to the priming mode shown in FIG. 6 where both the supply and vent conduits 16 and 24 are patent, and to an intermittent mode shown in FIG. 7 where the supply conduit 16 is occluded but the vent conduit 24 is patent. In the arrangement shown in FIGS. 5 through 7, the vertical or horizontal orientation of the control element 52 will act as a signal to medical care personnel located some distance from administration set, the operating state of the fluid control system 22. A vertically-oriented handle signals to the medical operator that both supply and vent conduits 16 and 24 are open. A horizontally-oriented control element 52 pointed toward either the supply or vent conduit 16 or 24 signals to the medical operator that the particular conduit is closed. While this particular alignment is preferred, as it is consistent with standard practice, or alignments are possible.

It should be noted that when referring to the "priming mode," the same mode is used to fill the burette chamber with a measured amount of fluid. In this case, the downstream clamp 40 would be closed to occlude the tubing 38 in FIG. 1 and the control element 52 rotated to the vertical position, as shown in FIG. 6. Air in the downstream conduit 38, the drip chamber 36, and the burette chamber 28 may leave these devices through the vent conduit 24 simultaneously with fluid entering these devices from the supply container 14. When the fluid level in the burette chamber reaches the level desired as indicated by the calibration marks 32 (FIG. 1), the control element is then rotated to occlude the supply conduit 16 as shown in FIG. 7. The vertical position of the control element 52 may also be thought of as a "measuring mode," or a "filling mode" in addition to the "priming mode." Although in the case shown in FIG. 1, only a downstream clamp 40 was used, the administration set 10 may alternatively, or in addition, be used with an infusion pump that would provide an occluding finger or device downstream from the drip chamber 36.

Now that the prescribed amount of fluid for the patent has been measured into the burette chamber 28, it can be administered when desired. In the case of FIG. 1, the downstream roller clamp can be opened and the fluid captured in the burette chamber 28 will begin gravity flow into the patient. As the fluid flows from the burette chamber 28 into the patient, air from the vent conduit 24 replaces the lost fluid simultaneously so that a partial vacuum is not formed within the burette. When the burette chamber empties, a floating ball 82 (FIG. 1) in the drip chamber 36 that floats at approximately the fluid level will stop further flow from the burette chamber by moving into a ball seat (not shown) at the bottom of the drip chamber. This ball and seat arrangement acts to prevent air from entering the downstream conduit 38. While a ball valve arrangement is shown and described, other means for stopping flow from an empty burette chamber are possible.

Figure 8:
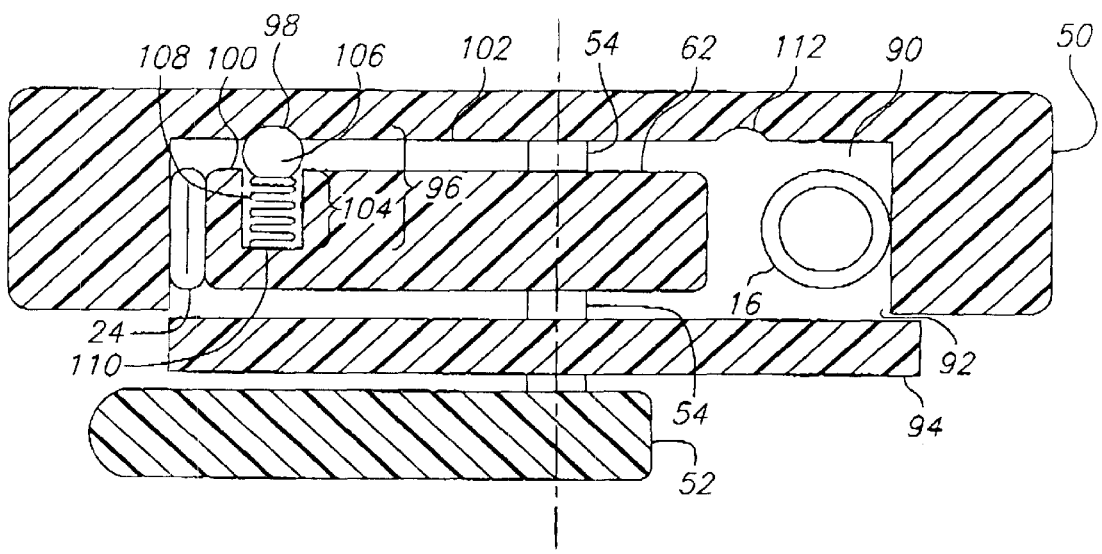
FIG. 8 is a top, partial-sectional view of a spring-loaded ball bearing/detent cam positioning system for positively locating the cam in relation to the fluid conduits.

Certain components of the fluid flow control system 22 are shown in further detail in FIG. 8. In one detailed arrangement of the fluid flow control system 22 shown in FIG. 8, the housing 50 includes a cavity 90 with an opening 92. The solid cam 62 is mounted through the opening 92 into the cavity 90 of the housing 50. In addition, the housing 50 includes a cover 94 that closes the opening 92 to the cavity 90. The cover 94 is located between the solid cam 62 and the control element 52, the control element being located outside the housing 50 for easy access.

The fluid flow control system 22 preferably includes a positioning device 96 that holds the solid cam 62 in a predetermined position or positions, such as at positions that will result in the fluid flow control system being in the priming, intermittent, and continuous flow modes. The positioning device 96 in the embodiment shown in FIG. 8 includes a detent 98 or indentation in either the inner surface 100 of the cam 62 or the inner housing surface 102 of the housing 50. This positioning device 96 may further include a spring-loaded aligning device 104 on the opposite surface to where the detent 98 is located. In one preferred arrangement, the spring-loaded aligning device 104 includes a ball bearing 106, and a spring 108. The spring 108 is attached within a cavity 110 formed in the inner surface 100 of the cam 62 in this embodiment. When the cavity 110 and the detent 98 are aligned, the spring 108 forces the ball bearing 106 into the detent 98. In that position, the ball bearing 106 is located partially in the cavity 110 of the cam and is partially within the detent 90 of the housing thereby temporarily locking the solid cam 62 in position in relation to the housing 50. The detent 98 is rounded with rounded edges and by applying a certain level of rotational force to the control element 52, the medical operator can overcome the locking force of the positioning device 96 and rotate the control element 52. Rotation of the control element will result in rotation of the solid cam 62 which will force the ball bearing 106 out of the detent 98 and farther into the channel 110 of the cam thereby compressing the spring 108. The cam may be rotated to another position where the ball bearing may engage a detent, such as the detent 112 one shown in FIG. 8 where the fluid flow control system would be in the intermittent mode.

The above positioning device provides not only for positive locking of the cam in a selected position so that it is not easily inadvertently moved out of the selected position, it also may provide a tactile sensation to the operator. The ball bearing moving into the detent may be felt by the operator and a higher level of comfort and confidence developed in that operator that the cam is in the desired position.

Figure 9:
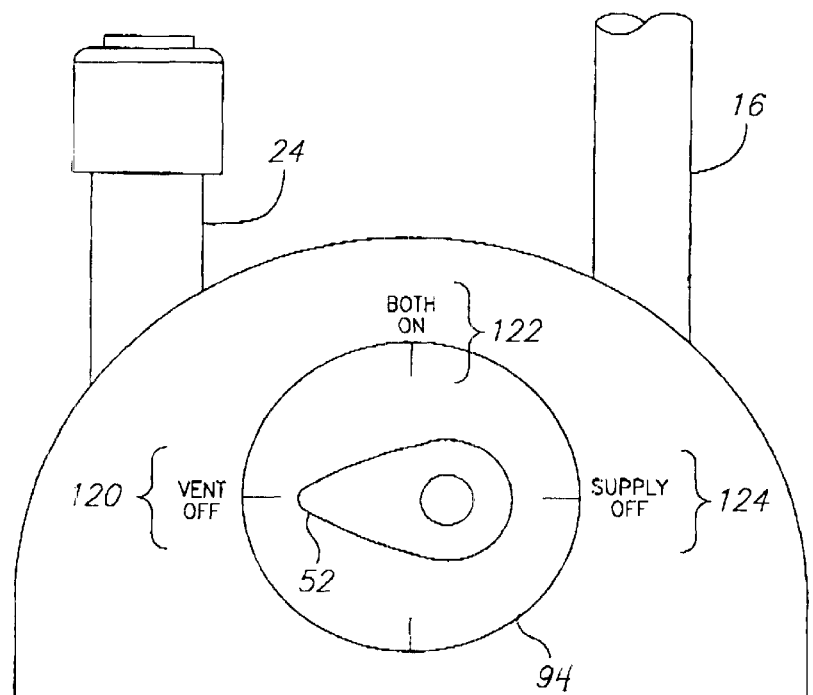
FIG. 9 is a front view of the upstream housing of a burette safety valve in accordance with an aspect of the invention showing the interaction of the cam control lever with three flow mode indicators so that the particular flow mode selected for the burette can be seen from a distance.
Figure 3:
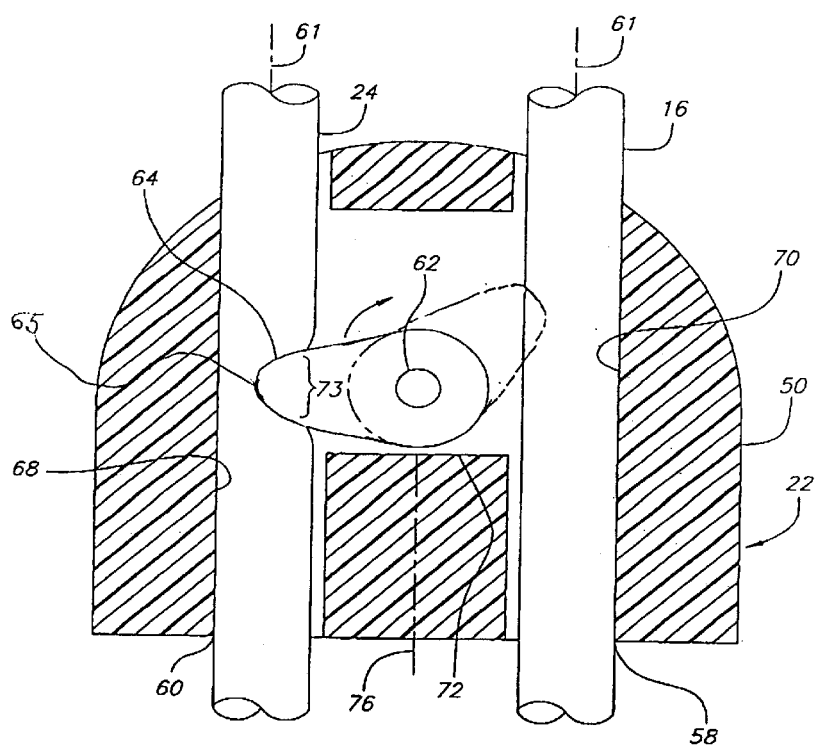
Figure 4:
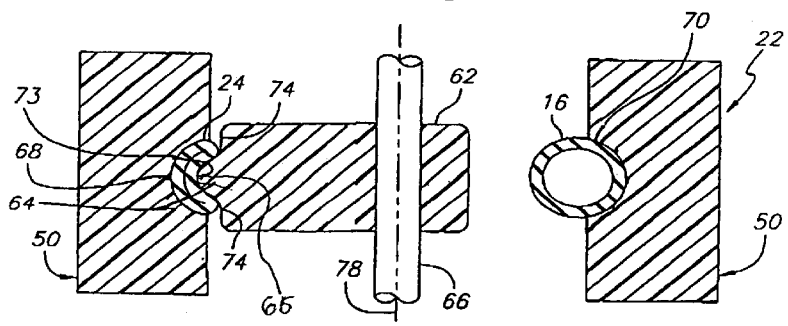
Figure 5:
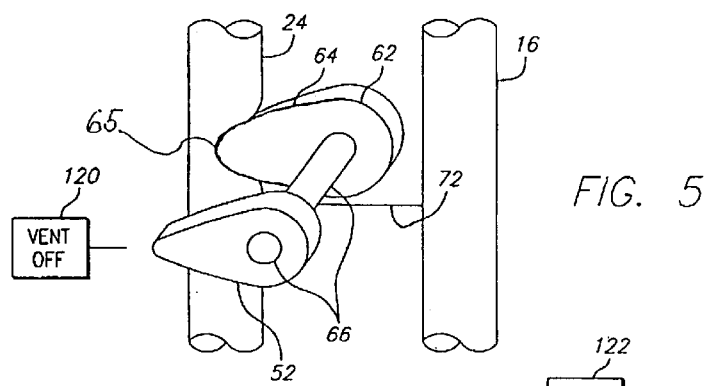
Figure 6:
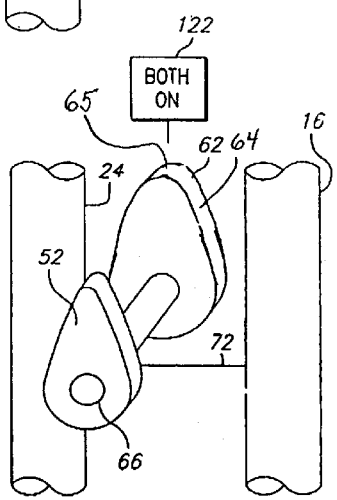
Figure 7:
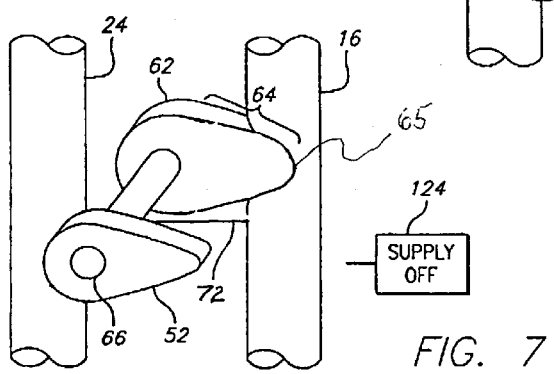

Referring now to FIG. 9, the exterior of the housing 50 includes three visual indicators; i.e., "VENT OFF" 120, "BOTH ON" 122, and "SUPPLY OFF" 124 designed to notify the medical operator of the operating state or flow mode of the fluid flow control system 22. The cover 94 may also include other visual indicators as needed. The visual indicators could be applied to the exterior surface of the cover 94 such as by inking or could be molded into the surface of the cover 94. The visual indicators 120, 122, and 124 may include labeling, coloring, and protrusions for quick and unambiguous recognition of the operating state or flow mode of the fluid flow control system 22. They may also include a phosphorescent material for viewing the operating state in darkness. As desired, light sources may be built in or other devices used for providing indication of the operating state.

In FIG. 9, three detents (not shown) exist for holding the solid cam 62 in three predetermined locations corresponding to the three flow modes discussed above. These are the continuous flow mode where the supply conduit 16 is open and the vent conduit 24 is closed as shown in FIG. 5, the priming flow mode where both conduits 16 and 24 are open, see FIG. 6, and the intermittent flow mode where the supply conduit 16 is closed and the vent conduit 24 is open as seen in FIG. 7. The use of spring-biased ball bearings and detents is only one arrangement that may be used to achieve a positive positioning of the cam in these or other locations. Other arrangements are possible.

From the foregoing, it will be appreciated that the fluid flow control system 22 in accordance with the principles of the invention provides a safer and more effective fluid flow control system 22 than previous single valved devices. By having a more positive engagement with the conduits and by having visual indicators notifying the medical operator from a distance of the operating state of the system, an improved fluid flow control system has been provided. By rounding the exposed surfaces, there is less likelihood of damage to the skin and gloves of the medical operator.

Different arrangements from those shown may be found to be useful. For example, the supply conduit 16 and the vent conduit 24 are shown as being mounted parallel to the longitudinal axis of the burette chamber. However, the conduits may actually be mounted at an angle to the axis in another arrangement. The housing 50 is shown has having a cavity 90 in FIG. 8. However, it may be formed of individual parts with no cavity but resulting in the same effect. Furthermore, different systems may be used to provide positive locking of the cam in desired positions.

While only the presently preferred embodiments have been described in detail, as will be apparent to those skilled in the art, modifications and improvements may be made to the device disclosed herein without departing from the scope of the invention. Accordingly, it is not intended that the invention be limited, except as by the appended claims.

What is claimed is:

1. A system for controlling fluid flow through multiple conduits, the system comprising:
   a housing in which the conduits are held in predetermined, fixed positions;
   a cam rotatably disposed within the housing and mounted so as to permit controlled, alternate compression contact of an external surface of the cam with each of the conduits to restrict flow therein, the cam configured so as to prevent simultaneous restriction of flow in each of the conduits; and
   a control element operably connected to the cam to selectively position the cam into contact with each of the conduits;
   wherein the housing secures the conduits against movement at positions both above and below the contact locations of the cam with the conduits.

2. The system of claim 1 wherein the cam is mounted so that it rotates about an axis that is perpendicular to longitudinal axes of the conduits.

3. The system of claim 1 wherein the housing receives the conduits so that the housing provides support for each conduit generally surrounding the area of compression contact with the cam.

4. The system of claim 1 wherein the cam is located between the conduits.

5. The system of claim 1 further comprising a stop surface disposed within the housing, the surface located to prevent the cam from rotating through a predetermined arc.

6. The system of claim 1 wherein the housing comprises a visual indicator visible from a position external to the housing to disclose the position of the cam in relation to the conduits.

7. The system of claim 1 wherein the control element comprises a handle disposed on the outside of the housing, the handle aligned with the cam in a predetermined manner to indicate the position of the cam.

8. The system of claim 7 wherein the handle is aligned with the cam to indicate a flow operating state of a conduit.

9. The system of claim 7 wherein the handle is aligned with the cam to indicate that a conduit is occluded.

10. The system of claim 7 further comprising an indicator disposed on the outside of the housing so that aligning the handle with the indicator discloses a flow operating state of a conduit.

11. The system of claim 1 further comprising a positioning device located within the housing for controllably holding the cam at a predetermined position.

12. The system of claim 11 wherein the positioning device comprises a detent.

13. The system of claim 12 wherein the positioning device further comprises a spring-loaded aligning device located on one of the cam or the housing and the detent is located on the other of the cam or the housing.

14. The system of claim 13 wherein the spring-loaded aligning device comprises a ball bearing, and a spring, the spring located so as to urge the ball bearing into the detent so that the cam will controllably remain in a predetermined position at the detent.

15. The system of claim 1 further comprising a plurality of positioning devices located within the housing for controllably holding the cam at predetermined positions in relation to the conduits.

16. The system of claim 1 wherein the cam is solid.

17. The system of claim 1 wherein the cam rotates about an axis located parallel to longitudinal axes of the conduits.

18. A medical burette having an upstream end and a downstream end interconnected by a burette chamber, the burette chamber having a longitudinal axis, the burette comprising:
   a housing disposed at the upstream end of the burette, the housing having a vent conduit, and a supply conduit, the conduits held in fixed positions within the housing and in fluid communication with the chamber;
   a cam rotatably mounted within the housing between the vent conduit and the supply conduit, the cam mounted within compression contact range of both the conduits such that the cam may selectively be rotated to occlude either of the conduits, the cam configured so as to prevent simultaneous restriction of flow in each of the conduits;
   a control element connected to the cam for rotating the cam to selectively occlude the conduits, the control element connected to the cam such that the control element has an indicator function of the position of the cam in regard to the occlusion of the conduits.

19. The medical burette of claim 18 wherein the cam is mounted so that it rotates about an axis that is perpendicular to longitudinal axes of the conduits.

20. The medical burette of claim 18 wherein the housing receives the conduits so that the housing provides support for each conduit generally surrounding the area of compression contact with the cam.

21. The medical burette of claim 18 wherein the housing comprises a stop surface located to prevent the cam from rotating through a predetermined arc.

22. The medical burette of claim 18 further comprising a positioning device located within the housing for controllably holding the cam at a predetermined position in relation to a conduit.

23. The medical burette of claim 22 wherein the positioning device comprises a detent.

24. The medical burette of claim 23 wherein the positioning device further comprises a spring-loaded aligning device located on one of the cam or the housing and the detent is located on the other of the cam or the housing.

25. The medical burette of claim 24 wherein the spring-loaded aligning device comprises a ball bearing, and a spring, the spring located so as to urge the ball bearing into the detent so that the cam will controllably remain in a predetermined position at the detent.

26. The medical burette of claim 17 further comprising a plurality of positioning devices located within the housing for controllably holding the cam at predetermined positions in relation to the conduits.

27. The medical burette of claim 17 wherein the cam is solid.

28. The medical burette of claim 17 wherein the cam rotates about an axis located parallel to longitudinal axes of the conduits.

29. The medical burette of claim 17 wherein the cam is mounted so that it may be rotated to a position at which neither conduit is occluded.

30. The medical burette of claim 17 further comprising indicators at an exterior surface of the housing, the indicators adapted to signal a state of fluid flow of the burette.

31. A method for controlling fluid flow through multiple conduits into a burette, the burette having a housing disposed at an upstream end, the method comprising:
    positioning the conduits in spaced-apart, fixed positions in the housing;
    rotating a cam disposed within the housing into alternate compressive contact of an external surface of the cam with each of the conduits to restrict flow therein, wherein simultaneous restriction of flow of each of the conduits is prevented; and
    controlling the rotation of the cam with an external control element; and
    securing the conduits against movement at positions both above and below the contact locations of the cam with the conduits.

32. The method of claim 31 wherein rotating the cam comprises rotating the cam about an axis that is perpendicular to longitudinal axes of the conduits.

33. The method of claim 31 wherein positioning the conduits comprises locating the conduits in the housing so that housing provides support for each conduit generally surrounding the area of compression contact with the cam.

34. The method of claim 31 further comprising the step of controllably holding the cam at a selected position such that inadvertent rotation of the cam from the selected position is resisted.

35. The method of claim 34 wherein the step of holding the cam comprises locating a positioning device partially within the housing and partially within the cam such that rotation of the cam is resisted.

36. The method of claim 35 further comprising biasing the positioning device into the location partially within the housing and partially within the cam.

37. The method of claim 31 wherein rotating the cam comprises rotating the cam about an axis that is parallel to longitudinal axes of the conduits.

38. The method of claim 31 further comprising indicating at an exterior surface of the housing the state of fluid flow of the burette.

* * * * *

UNITED STATES PATENT AND TRADEMARK OFFICE
CERTIFICATE OF CORRECTION

PATENT NO.    : 6,554,806 B2
DATED         : April 29, 2003
INVENTOR(S)   : Robert D. Butterfield and Emmet B. Anderson It is certified that error appears in the above-identified patent and that said Letters Patent is hereby corrected as shown below:

Drawings,
Replace Sheets 3 of 5 and Sheet 4 of 5 with attached Sheet 3 of 5 and Sheet 4 of 5 which add item [56] to FIGs. 3, 4, 5, 6 and 7.

Column 7,
Line 59, "cam 65", should read -- cam 62 --.

Signed and Sealed this

Ninth Day of September, 2003

JAMES E. ROGAN
*Director of the United States Patent and Trademark Office*